United States Patent [19]
Mori et al.

[11] Patent Number: 5,506,879
[45] Date of Patent: Apr. 9, 1996

[54] PLANIGRAPHIC X-RAY APPARATUS

[75] Inventors: Keisuke Mori; Kozo Nakano; Eiichi Arai; Takahiro Yoshimura; Masanori Otsuka; Kouichi Sonobe; Minoru Watanabe; Takashi Bessho; Kazuyuki Fujita, all of Kyoto, Japan

[73] Assignee: Kabushiki Kaisha Morita Seisakusho, Kyoto, Japan

[21] Appl. No.: 332,716

[22] Filed: Nov. 1, 1994

[30] Foreign Application Priority Data

Nov. 12, 1993 [JP] Japan ................................. 5-307170

[51] Int. Cl.⁶ .................................................. A61B 6/14
[52] U.S. Cl. ............................... 378/39; 378/38; 378/40
[58] Field of Search ........................... 378/38–40, 21, 378/25, 27, 115, 193, 195–197

[56] References Cited

U.S. PATENT DOCUMENTS 5,355,398 10/1994 Nakano et al. ..................... 378/38 X

*Primary Examiner*—David P. Porta
*Attorney, Agent, or Firm*—Koda and Androlia

[57] ABSTRACT

A planigraphic X-ray apparatus comprising a rotation mechanism for rotating a support member which supports an X-ray generator and an X-ray detection surface to rotate the X-ray generator and the X-ray detection surface around a subject, a position adjustment mechanism for setting the position of the rotation center of the support member rotated by the rotation mechanism and a linear movement means for moving the support member in the direction approximately perpendicular to the direction of the X-ray irradiated from the X-ray generator, whereby the X-ray detection surface is driven in the direction opposite to the movement of the linear movement means and the X-ray generator is rotated toward the X-ray detection surface in synchronization with the movement of the linear movement means. The position adjustment mechanism and the rotation mechanism are used only to set the position and direction of the support member with respect to the subject, and planigraphic photographing is possible only by moving the support member using a linear movement means exclusively provided for the support member, thereby facilitating the positioning operation of the support member with respect to a given planigraphic plane, simplifying the control program and making the entire apparatus compact and inexpensive.

8 Claims, 16 Drawing Sheets

PLANIGRAPHIC X-RAY APPARATUS

BACKGROUND OF THE INVENTION

1. Field of the Invention

The present invention relates to improvements in an X-ray apparatus for medical diagnosis, for example, dental and otolaryngological diagnosis, and more particularly to improvements in an X-ray apparatus for photographing planigraphic planes.

2. Prior Art

X-ray apparatuses for photographing tomographic planes of human heads, faces and jaws are known for medical diagnosis, for example, dental and otolaryngological diagnosis. In particular, rotational tomographic X-ray apparatuses for photographing dental arches have been used widely at small dental clinics as dental panoramic X-ray apparatuses. These days, in addition to the rotational tomographic X-ray apparatuses, there is an increase in demand for planigraphic X-ray apparatuses capable of selectively photographing specific regions, such as temporomandibular joints and dental implants, at narrow tomographic widths.

In view of increasing demands, the applicant of the present invention has proposed a rotational tomographic X-ray apparatus with a planigraphic function as Japanese Patent Application No. 4-139888 (Japanese Laid-Open Patent Publication No. 6-181). This apparatus is basically the panoramic X-ray apparatus additionally equipped with a planigraphic function. The apparatus is capable of performing clear planigraphic photographing without causing any distortion, equipped with a function for changing the magnifying ratios of X-ray images and is relatively compact and inexpensive enough to allow easy introduction to small clinics.

To perform planigraphic photographing, it is necessary to dispose an X-ray generator and an X-ray detection surface disposed opposite to each other with a subject positioned therebetween while maintaining a constant relationship, and to move the X-ray generator and the X-ray detection surface in parallel to the planigraphic plane selected to be photographed inside the subject and in directions opposite to each other. For this purpose, in the proposed apparatus, a rotary arm supporting the X-ray generator and the X-ray detection surface is linearly moved by using a position adjustment mechanism such an X-Y table provided for the panoramic X-ray apparatus, or the rotary arm is moved together with a position adjustment mechanism and an arm rotation mechanism as a whole system by using a linear movement mechanism of a different type.

However, when using a position adjustment mechanism, it is necessary to place the subject, or patient, in a predetermined direction in view of the directions of the position adjustment mechanism and the planigraphic plane to be photographed so as to move the X-ray generator and the X-ray detection surface in parallel with the planigraphic plane. This makes the first setting of the apparatus troublesome. Even though the movement parallel to the planigraphic plane can be obtained by placing the patient in a given direction and by combining the movements of the position adjustment mechanism in all dimensions, the control program to be used for this case becomes very complicated. In the case of a whole system which is moved by using a linear mechanism of a different type, the weight of the movable section becomes large, thereby causing the problems of making the linear movement mechanism large and expensive.

SUMMARY OF THE INVENTION

In view of the foregoing problems, it is an object of the present invention to provide an easy-to-use, relatively compact planigraphic X-ray apparatus.

To accomplish the object, the planigraphic X-ray apparatus of the present invention comprises a rotation mechanism for rotating a support member so that an X-ray generator and an X-ray detection surface, both being supported by the support member, can be rotated around a subject, a position adjustment mechanism for setting the position of the rotation center of the support member rotated by the rotation mechanism, a linear movement means for moving the support member in parallel with the planigraphic plane selected to be photographed inside the subject, an X-ray detection surface drive means for driving the X-ray detection surface in the direction opposite to the movement of the linear movement means and in synchronization with the movement thereof, and an X-ray generator rotation means for rotating the X-ray generator toward the X-ray detection surface in synchronization with the movement of the linear movement means.

The X-ray detection surface drive means can be accomplished by driving the X-ray detection surface by transmitting the rotation of the drive motor of the linear movement means via a mechanical synchronization mechanism, or by driving the X-ray detection surface using a motor driven at a rotation speed specifically proportional to the rotating speed of the drive motor of the linear movement means.

In addition, the X-ray generator rotation means can be accomplished by rotating the X-ray generator by transmitting the rotation of the drive motor of the linear movement means via a mechanical synchronization mechanism, or by detecting the position of the X-ray detection surface and the rotation angle of the X-ray generator with respect to the support member and by rotating the X-ray generator by driving a motor so that a predetermined relationship can be established between the detected position and angle. Furthermore, the X-ray generator can be rotated by driving a motor so that a predetermined rotation angle calculated from the detection position can be obtained.

Moreover, one of the X-ray detection surface drive means can be combined appropriately with one of the X-ray generator rotation means. For example, an X-ray detection surface drive means for driving the X-ray detection surface by using a motor driven at a rotation speed specifically proportional to the rotation speed of the drive motor of the linear movement means can be combined with an X-ray generator rotation means for rotating the X-ray generator by driving a motor so that the position of the X-ray detection surface with respect to the support member can be detected and a predetermined rotation angle calculated from the detection position can be obtained.

In addition, without activating the linear movement means for moving the support member and the X-ray generator rotation means for rotating the X-ray generator, by rotating the support member by using a rotation mechanism to rotate the X-ray generator and the X-ray detection surface, by controlling the position of the rotation center of the support member rotated by the position adjustment mechanism and by moving the X-ray detection surface in the direction approximately perpendicular to the direction of the X-ray irradiated from the X-ray generator in synchronization with the rotation of the support member, the apparatus of the present invention can have the function of photographing rotational tomographic planes in the same way as a conventional panoramic X-ray apparatus.

With this invention, the position adjustment mechanism and the rotation mechanism are used only to set the position and direction of the subject. At the time of planigraphic photographing, the support member can be moved by a linear movement means exclusively provided for the support member. In other words, after properly setting the position of the rotation center of the support member with respect to the planigraphic plane to be photographed, the setting of the apparatus can be completed only by rotating the support member so that the direction of the support member is appropriate with respect to the planigraphic plane. The support member can thus be easily positioned with respect to a given planigraphic plane and control of the apparatus can be simple. In addition, since the linear movement means is required only to support the weight of the support member and the weight of the X-ray generator with the X-ray detection surface mounted thereon, the linear movement means can be made relatively compact and low in cost.

When the apparatus is additionally provided with a function to photograph rotational tomographic planes, the apparatus can perform both rotational tomographic photographing and planigraphic photographing, thereby providing a superior X-ray apparatus suited for medical diagnosis.

DETAILED DESCRIPTION OF THE INVENTION

Figure 1:
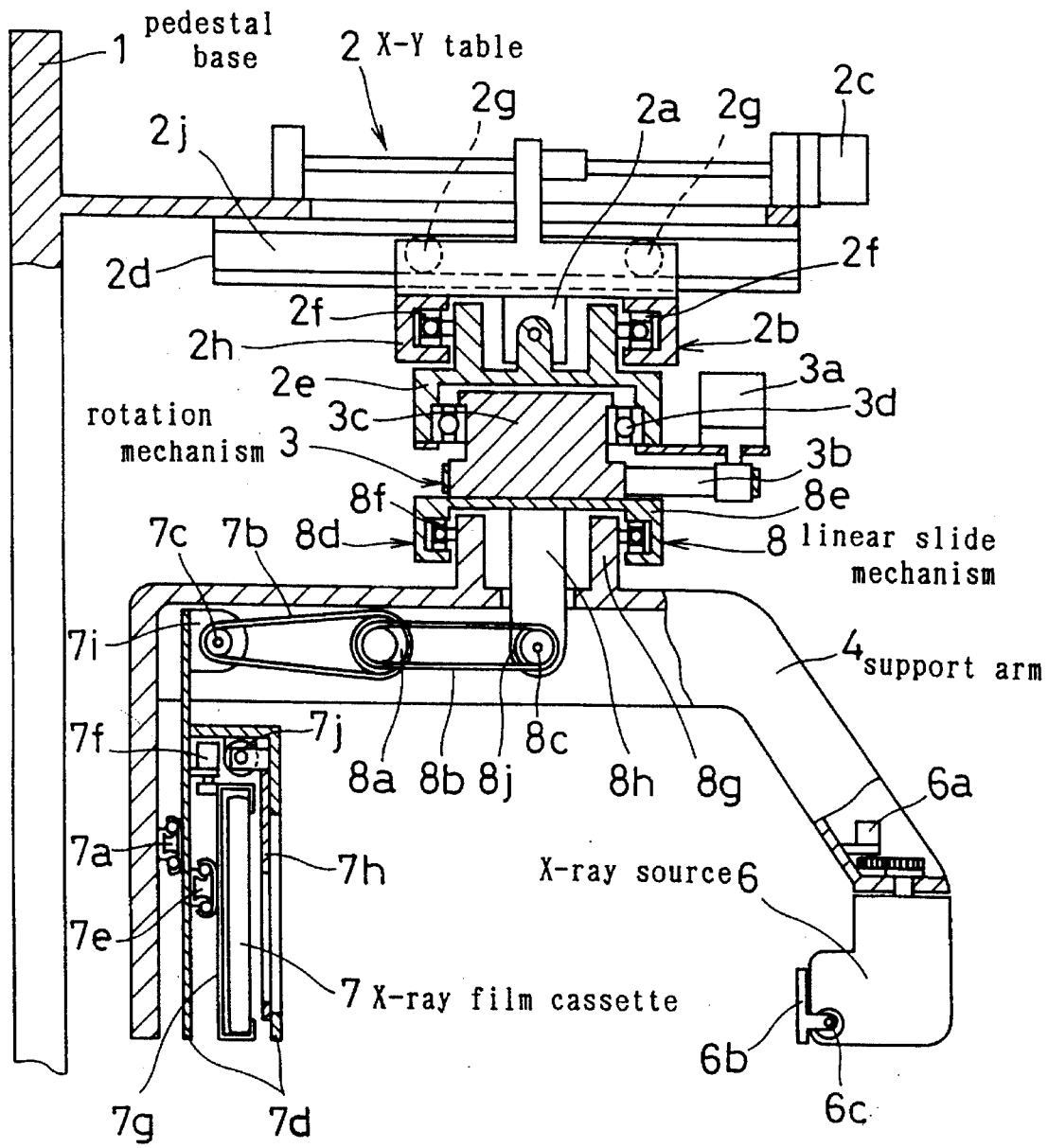
FIG. 1 is a fragmentary sectional side view illustrating the main section of an embodiment of an apparatus in accordance with the present invention.
Figure 2:
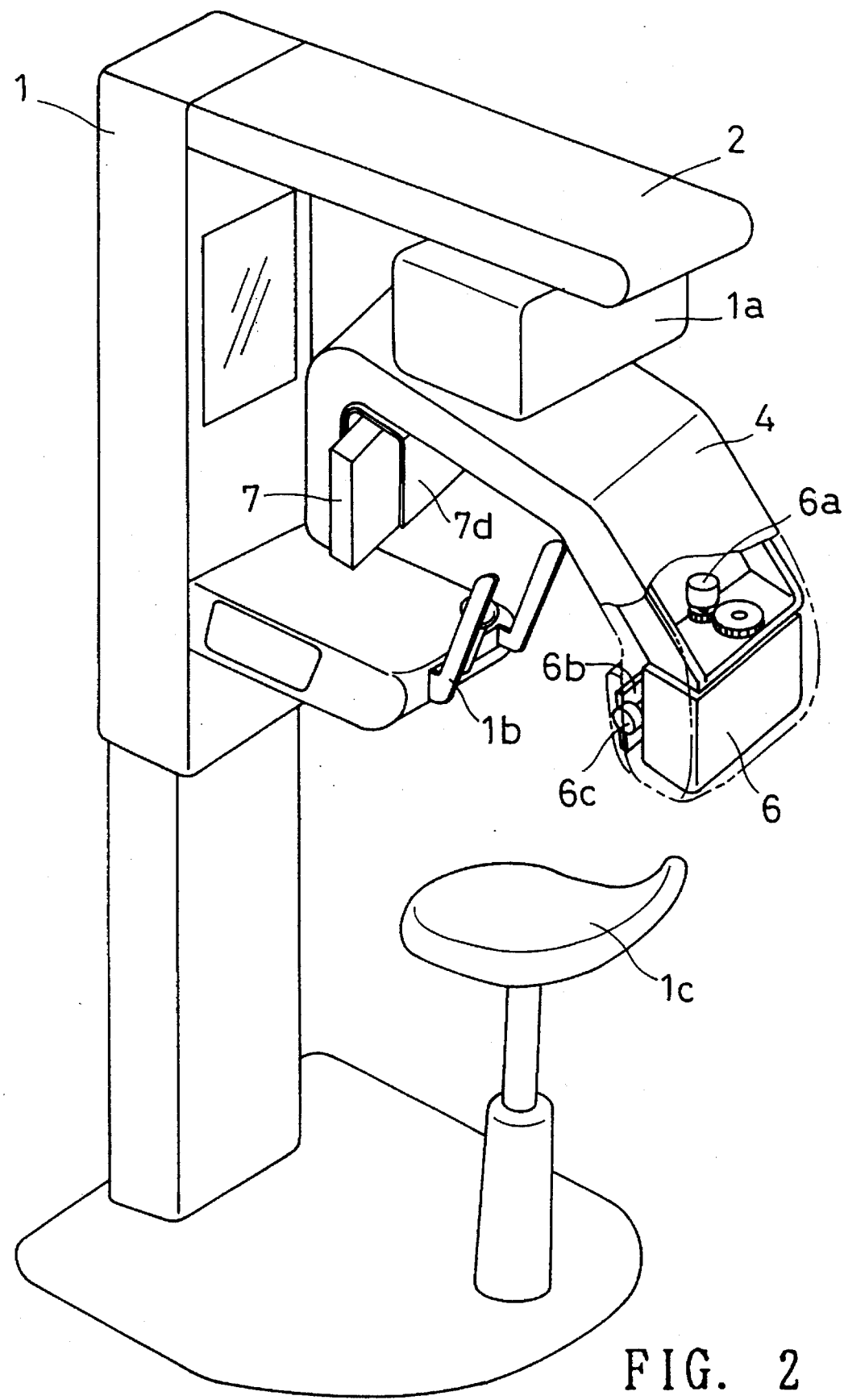
FIG. 2 is a fragmentary sectional perspective view illustrating the entire structure of the embodiment.
Figure 3:
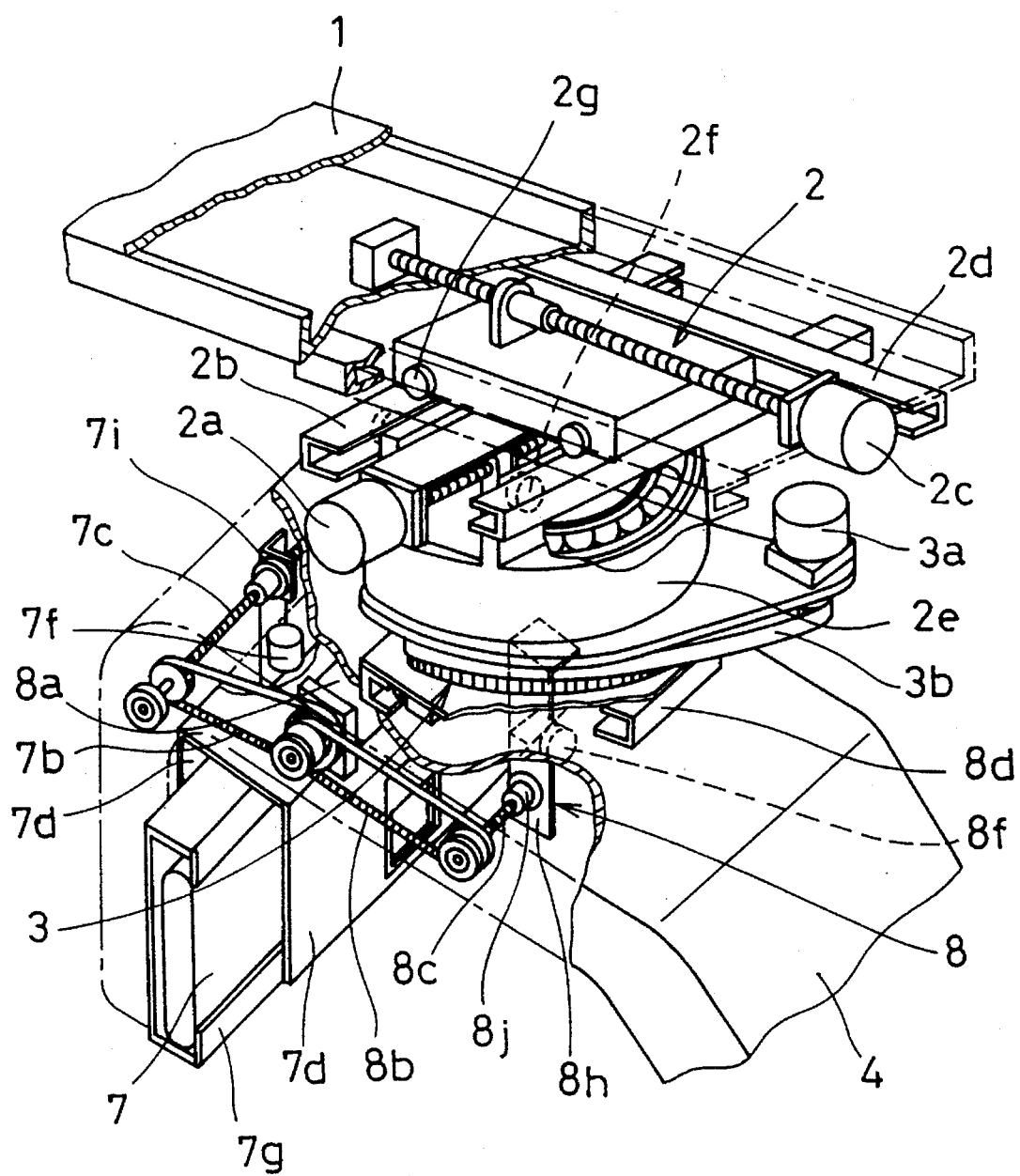
FIG. 3 is a fragmentary sectional perspective view illustrating the main section of the embodiment.

The embodiments shown in the figures will be explained below. FIGS. 1 to 3 are views illustrating an embodiment of an apparatus of the present invention. Referring to the figures, numeral 1 represents a pedestal base and numeral 2 represents an X-Y table used as a position adjustment mechanism for setting the position of the rotation center of a support member which is rotated in the condition wherein an X-ray generator is disposed opposite to an X-ray detection surface with a subject positioned therebetween. Numeral 3 represents the rotation mechanism of the support member and numeral 4 represents a support arm which corresponds to the support member. The support arm 4 is supported by the pedestal base 1 via the X-Y table 2 and the rotation mechanism 3. Numeral 6 represents an X-ray source which corresponds to the X-ray generator and numeral 7 represents an X-ray film cassette which corresponds to the X-ray detection surface. Numeral 8 represents a linear slide movement mechanism disposed as a linear movement means for the support arm 4. The X-ray source 6 is disposed at one end of the support arm 4 and the X-ray film cassette 7 is disposed at the other end thereof in an opposite relation to each other.

The X-Y table 2 comprises an X-axis motor 2a and a guide mechanism 2b for adjusting the position of the table in the X direction, a Y-axis motor 2c and a guide mechanism 2d for adjusting the position of the table in the Y direction, and a slide member 2e. Driven by the motors 2a and 2c, the slide member 2e is moved in the X-Y plane and the position of the rotation mechanism 3 disposed at the lower section of the slide member 2e is controlled. The guide mechanisms 2b and 2d comprise rollers 2f, 2g rotatable via bearings and guide frames 2h, 2j equipped with guide grooves for these rollers, respectively.

The rotation mechanism 3 comprises a rotation motor 3a and a belt mechanism 3b constructed of a pulley and a belt for transmitting the rotation of the motor, and a rotation member 3c driven by the belt mechanism 3b. The rotation member 3c is rotatably supported by the slide member 2e of the X-Y table 2 via a bearing 3d. Accordingly, the rotation member 3c is rotated by driving the motor 3a, and the support arm 4 disposed at the lower section of the rotation member 3c is also rotated simultaneously.

The linear slide mechanism 8 comprises a drive motor 8a, a movement screw shaft 8c driven by a belt mechanism 8b for transmitting the rotation of the motor 8a and a guide mechanism 8d. The drive motor 8a is secured to the support arm 4 and the movement screw shaft 8c is rotatably disposed on the support arm 4. The guide mechanism 8d comprises a guide frame 8e disposed on the rotation member 3c and a slide member 8g integrally formed on the top surface of the support arm 4 and supported by the guide frame 8e via rollers 8f. A connection member 8h is integrally secured to the bottom surface of the guide frame 8e. The movement screw shaft 8c is threadedly engaged with a female screw member 8j disposed at the lower end of the connection member 8h. When rotated, the movement screw shaft 8c is moved relative to the female screw member 8j in the axial direction.

With this structure, the direction of movement by the guide frame 8e can be set in parallel to a given planigraphic plane by rotating the support arm 4 and the entire linear slide mechanism 8 constructed of the guide frame 8e and other elements by using the rotation mechanism 3. By driving the motor 8a in this condition, the support arm 4 can be moved linearly along the guide frame 8e (in the direction perpendicular to the paper surface in the case of the example shown in FIG. 1).

The support arm 4 is provided with a rotation motor 6a for rotating the X-ray source 6 with respect to the support arm 4 and is structured to rotate around the vertical axis thereof in synchronization with the movement of the support arm 4 so that the X-ray is always irradiated to the X-ray film cassette 7. This rotation control will be described later.

Furthermore, a housing 7d supported by the support arm 4 via a slide mechanism 7a is disposed on the side of the X-ray film cassette 7. In this housing 7d, a holder 7g is disposed, which is supported by a slide mechanism 7e and moved by a drive motor 7f. The X-ray film cassette 7 is accommodated in this holder 7g. A belt mechanism 7b for transmitting the rotation of the drive motor 8a and a movement screw shaft 7c rotated by the belt mechanism 7b are disposed over the housing 7d. A slide member 7i secured to the housing 7d is threadedly engaged with the movement screw shaft 7c. Accordingly, when the support arm 4 is moved by the drive motor 8a, in synchronization with this movement the slide member 7i, that is, the housing 7d is moved together with the X-ray film cassette 7 in the direction opposite to the movement direction of the support arm 4.

Since the embodiment of the apparatus in accordance with the present invention is structured by adding the linear slide mechanism 8 to a conventional panoramic X-ray apparatus and is provided as an apparatus capable of performing planigraphic photographing as well as rotational tomographic photographing, the irradiation field shape of the X-ray from the X-ray source 6 and the beam-receiving shape of the X-ray film cassette 7 must be changed depending on the purpose of photographing. To accomplish the change, an irradiation field shape changeover plate 6b and a drive motor 6c for driving the plate are provided in the X-ray source 6, and on the cassette side, a beam-receiving shape changeover plate 7h and a drive motor 6c for driving the plate are provided.

Referring to FIG. 2, numeral 1a represents a support unit for accommodating the X-axis mechanisms such as the X-axis motor 2a and the guide mechanism 2b for the X-Y table 2 and the rotation mechanism 3. In addition, numeral 1b represents a mechanism for securing the head of a patient disposed between the X-ray source 6 and the X-ray film cassette 7, and numeral 1c represents a chair for the patient. The height of the pedestal base 1 can be adjusted as desired depending on the sitting height of the patient seated on the chair 1c. These mechanisms adopted for the embodiment are similar to those for a conventional dental panoramic X-ray apparatus.

Figure 4:
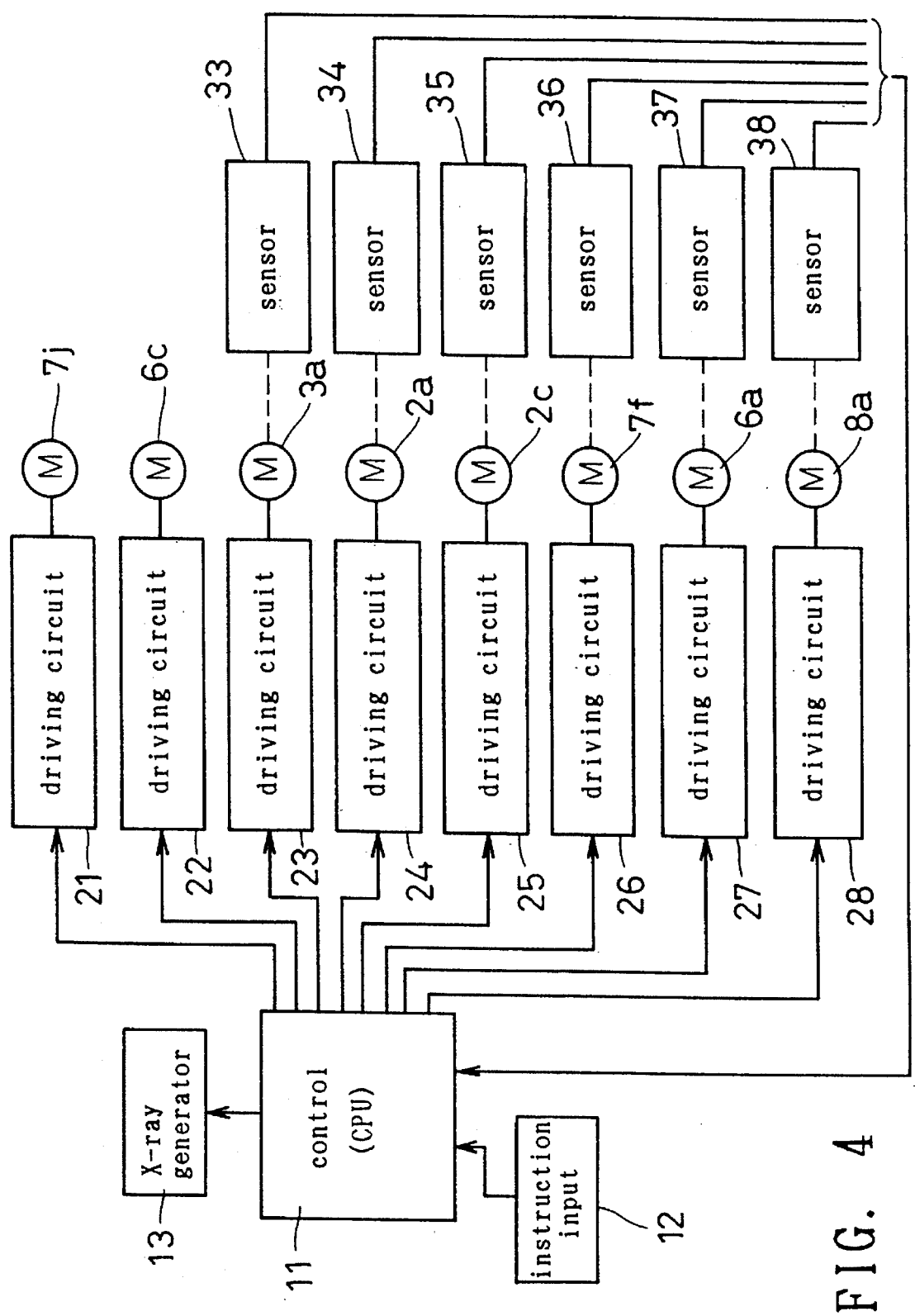
FIG. 4 is a block diagram illustrating the drive circuits of the embodiment.

FIG. 4 shows the drive circuits of the embodiment of the present invention. Numeral 11 represents a control section including a CPU, numeral 12 represents an operation instruction input circuit, numeral 13 represents an X-ray generator circuit, numerals 21 to 28 represent drive circuits for various motors, numerals 33 to 38 represent sensors for detecting positions and angles of various sections of the embodiment. When the operator of the apparatus inputs an instruction for designating a photographing mode by operating the operation instruction input circuit 12, predetermined signals are output from the control section 11 to the drive circuits depending on the photographing mode (planigraphic photographing mode or rotational tomographic photographing mode). The motors are thus driven and the results of motor operation are detected by the sensors and fed back to the control section 11. Since the number of motors is changed depending on the drive system as described later, the drive circuits and the sensors are disposed accordingly.

Figure 5:
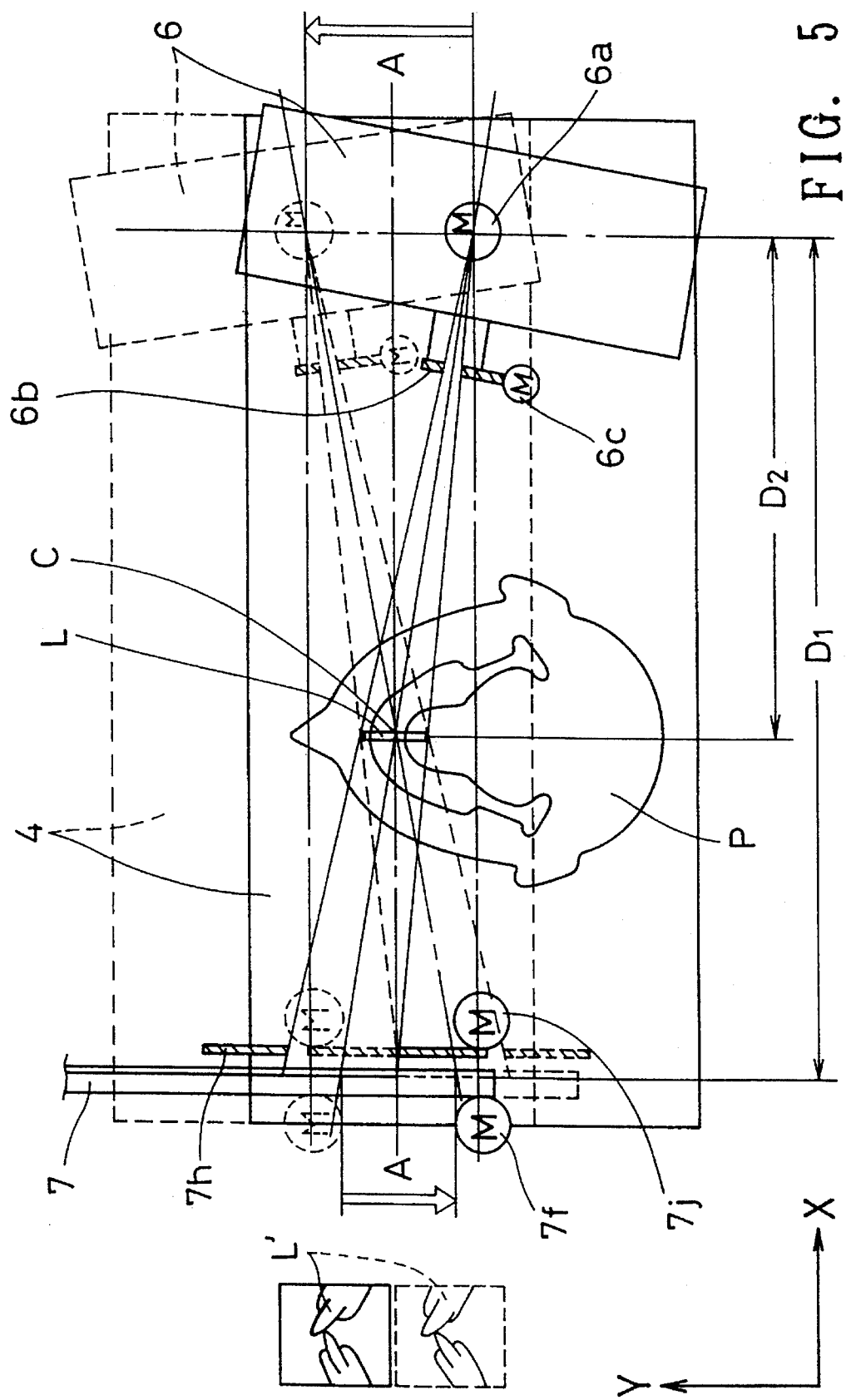
FIG. 5 is a view illustrating planigraphic photographing performed by the embodiment.

By using the apparatus described above, planigraphic photographing is performed as described below. The description given below applies to the case wherein the central back-and-forth plane of the front tooth section is selected as a planigraphic plane L. Referring to FIG. 5, reference character P represents a subject, that is, the head of a patient. First, the patient is seated on the chair 1c and his head is secured between the X-ray source 6 and the X-ray film cassette 7. The position of the support arm 4 in the horizontal plane is adjusted by the X-Y table 2 and the direction of the support arm 4 is adjusted by the rotation mechanism 3 so that the longitudinal direction of the support arm 4 is aligned with center line A—A which is perpendicular to the planigraphic plane L.

In this case, the adjustment of the angle of the support arm 4 is particularly important, since the movement direction of the support arm 4 must be parallel to the planigraphic plane L. However, since the angle can be set by the rotation mechanism 3 as desired, it is not necessary to direct the patient to a specific direction. This adjustment operation can thus be done easily. Furthermore, since the magnifying ratio of the X-ray image to be obtained is determined by the ratio of the distance $D_1$ between the X-ray source 6 and the X-ray film cassette 7 to the distance $D_2$ between the X-ray source 6 and the planigraphic plane L, the position of the support arm 4 can be set appropriately so that a desired magnifying ratio can be obtained. After these adjustments, the X-Y table 2 and the rotation mechanism 3 are not required to be operated and remain stationary.

At the time of photographing, the linear slide mechanism 8 linearly moves the support arm 4 so that the X-ray source 6 can move from the position indicated by the solid lines slightly away from the center line A—A to the position indicated by the broken lines beyond center line A—A as shown by the arrow indicated on the X-ray generator side. In synchronization with this movement, the X-ray film cassette 7 is moved in parallel from the position indicated by the broken lines in the direction opposite to that of the X-ray source 6 as shown by the arrow indicated on the film cassette side. In accordance with this movement, the X-ray source 6 is rotated so that the central axis of the X-ray beam always passes center C of the planigraphic plane L and is incident on the same position of the X-ray film cassette 7.

By this control, the X-ray image of the same region of the planigraphic plane L is always formed at the same position of the film cassette 7. On the other hand, the X-ray images other than that of the region are moved along the film surface, resulting in blurred images. Consequently, the X-ray image L' of the planigraphic plane L can be photographed. To obtain clearer X-ray images, the amount of the movement should preferably be larger. The range of the movement is not always necessary to be symmetrical with respect to line A—A. The irradiation field shape of the X-ray source 6 and the beam-receiving shape of the X-ray film cassette 7 are changed automatically to the shapes and sizes required for planigraphic photographing by using the irradiation field shape changeover plate 6b and the beam-receiving shape changeover plate 7h.

The embodiment of the apparatus of the present invention can also perform rotational tomographic photographing, with the linear slide mechanism 8 unoperated, that is, remained stationary. In other words, without driving the motor 8a, the apparatus can perform rotational tomographic photographing in the same way as general panoramic X-ray apparatuses. More particularly, the support arm 4 is rotated by the rotation mechanism 3 while the position of the rotation axis is controlled by the X-Y table, and in synchronization with this rotation the X-ray film cassette 7 is moved by the drive motor 7f in the direction approximately perpendicular to the direction of the X-ray irradiated from the X-ray source 6. At this time, the irradiation field shape of the X-ray source 6 and the beam-receiving shape of the X-ray film cassette 7 are changed automatically to vertical slit shapes required for panoramic photographing by using the irradiation field shape changeover plate 6b and the beam-receiving shape changeover plate 7h.

Figure 6:
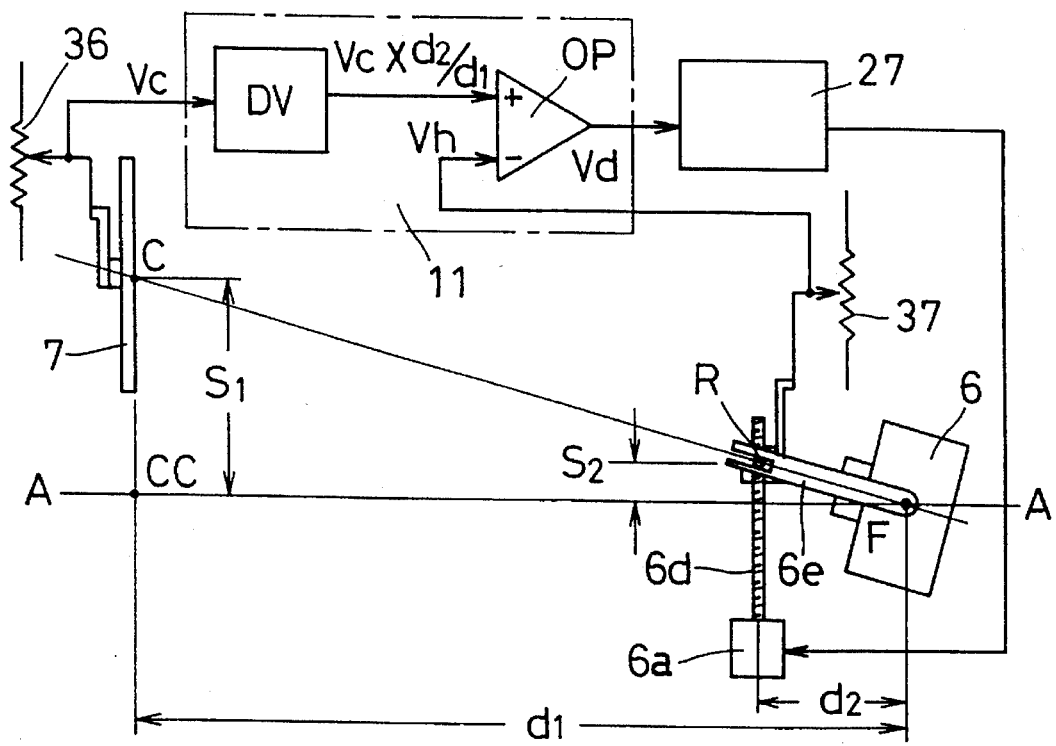
FIGS. 6 and 7 are views illustrating the control operation of the X-ray source and the film cassette of the embodiment.

Next, the control regarding the rotation of the X-ray source 6 and the movement of the X-ray film cassette 7, particularly important for planigraphic photographing, is described below. FIG. 6 is a view illustrating the basic relationship between the direction of the X-ray source 6 and the position of the X-ray film cassette 7. The following descriptions are given supposing that the rotation of the rotation motor 6a is transmitted to the X-ray source 6 rotatably disposed on the support arm via a movement screw shall 6d and a rotation arm 6e. Referring to the figure, the rotation arm 6e is projected toward the X-ray film cassette 7. However, even if it is projected in the opposite direction, it operates on the same principle.

As described earlier, in the case of planigraphic photographing, the direction of the X-ray source 6 must be controlled so that the X-ray can always be irradiated to the X-ray film cassette 7 in synchronization with the movement of the support arm 4. This control is accomplished as described below. Assuming that the distance between position CC of the X-ray film cassette 7 on center line A—A and focus F of the X-ray source 6 is $d_1$, the distance between focus F and connection point R of the rotation arm 6e is $d_2$, the distance between center line A—A and center point C of the X-ray film cassette 7 at a certain moment is $s_1$ and the distance between center line A—A and connection point R of the rotation arm 6e is $s_2$, these distances are proportional and constitute similar triangles. Accordingly, $s_1/s_2 = d_1/d_2$ is obtained and $s_2 = s_1 \times d_2/d_1$ is always established.

Accordingly, the position of the X-ray film cassette 7 is detected by a cassette position sensor 36 and the position of connection point R is detected by an X-ray source angle sensor 37, and based on the results of the detection, the rotation motor 6a is feedback-controlled to satisfy the above conditions. As a result, the direction of the X-ray source 6 is controlled so that the X-ray can always be irradiated to the X-ray film cassette 7.

For example, when the sensors 36 and 37 have the same stroke, the voltage of detection signal Vc of the sensor 36 is divided by voltage divider DV in accordance with $d_2/d_1$ and the resultant voltage is compared with detection signal Vh of the sensor 37 by error amp OP. Error voltage Vd obtained in this way is used to drive a drive circuit 27, thereby activating the rotation motor 6a. Consequently, the entire circuit functions so that error voltage Vd is always zero. The relationship required for the planigraphic photographing can thus be established between the X-ray source 6 and the X-ray film cassette 7. If the voltage dividing ratio of voltage divider DV is set to satisfy $s_2 = s_1 \times d_2/d_1$, the sensors 36 and 37 are not required to have the same stroke. In this case, the sensor 37 on the side of the X-ray source 6, which must be installed in a relatively limited space, can be made smaller.

Figure 7:
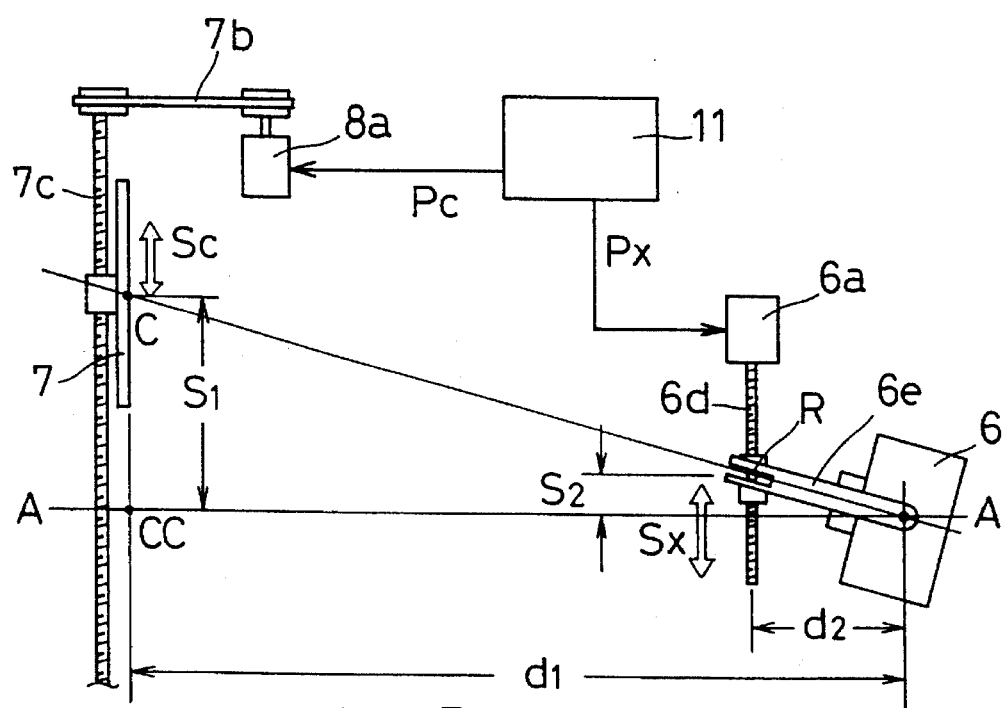

FIG. 7 shows an example wherein the X-ray film cassette 7 is mechanically synchronized by the drive motor 8a of the linear slide mechanism 8, and this drive motor 8a and the rotation motor 6a of the X-ray source 6 are controlled by the open loop control method. More particularly, assuming that the movement speed of the X-ray film cassette 7 is Sc and the movement speed of connection point R of the X-ray source 6 is Sx, the motors 8a and 6a are driven so that $Sc/Sx = d_1/d_2$ is established. As a result, the direction of the X-ray source 6 is controlled so that the X-ray can always be irradiated to the X-ray film cassette 7.

For example, when stepping motors are used for the motors and their reduction gear ratios are the same, control can be accomplished by selecting the number of drive pulses for each motor so that the relationship of $Sx = Sc \times d_2/d_1$ can be established. Accordingly, assuming that the pulse frequency of the rotation motor 6a is Px and that of the drive motor 8a is Pc, control is performed by the control section 11 in accordance with the relationship of $Px = Pc \times d_2/d_1$. The X-ray film cassette 7 can also be driven by an exclusively provided motor for example as described later referring to FIG. 10. In this case, the drive control can be performed in a way similar to that described above.

A variety of mechanisms and systems are possible to drive the linear slide mechanism 8 and the X-ray film cassette 7 and to rotate the X-ray source 6 at the same time. These mechanisms and systems are shown in FIGS. 8 to 13.

Figure 8:
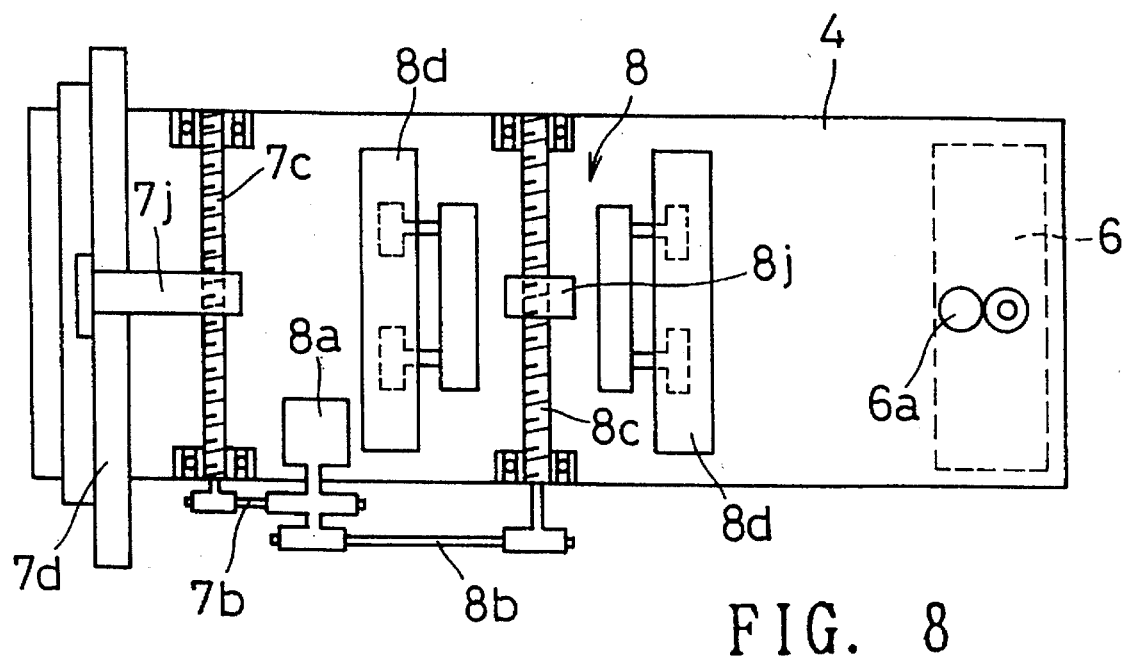
FIGS. 8 to 13 are schematic plan views illustrating the drive mechanisms of the X-ray source and the film cassette of the embodiment.

FIG. 8 shows the mechanism and system for the embodiment described referring to FIGS. 1 to 3. The linear slide mechanism 8 comprises drive motor 8a, belt mechanism 8b, movement screw shaft 8c and guide mechanism 8d. The support arm 4 is moved by driving the motor 8a. The belt drive mechanism 7b and the movement screw shaft 7c are provided on the side of the X-ray film cassette 7. The housing 7d accommodating the X-ray film cassette 7 is moved by the rotation of the drive motor 8a of the linear slide mechanism 8. In addition, the rotation motor 6a of the X-ray source 6 is electrically controlled as described earlier referring to FIGS. 6 and 7 so that the rotation angle of the X-ray source 6 can be changed in synchronization with the movement of the support arm 4.

Figure 9:
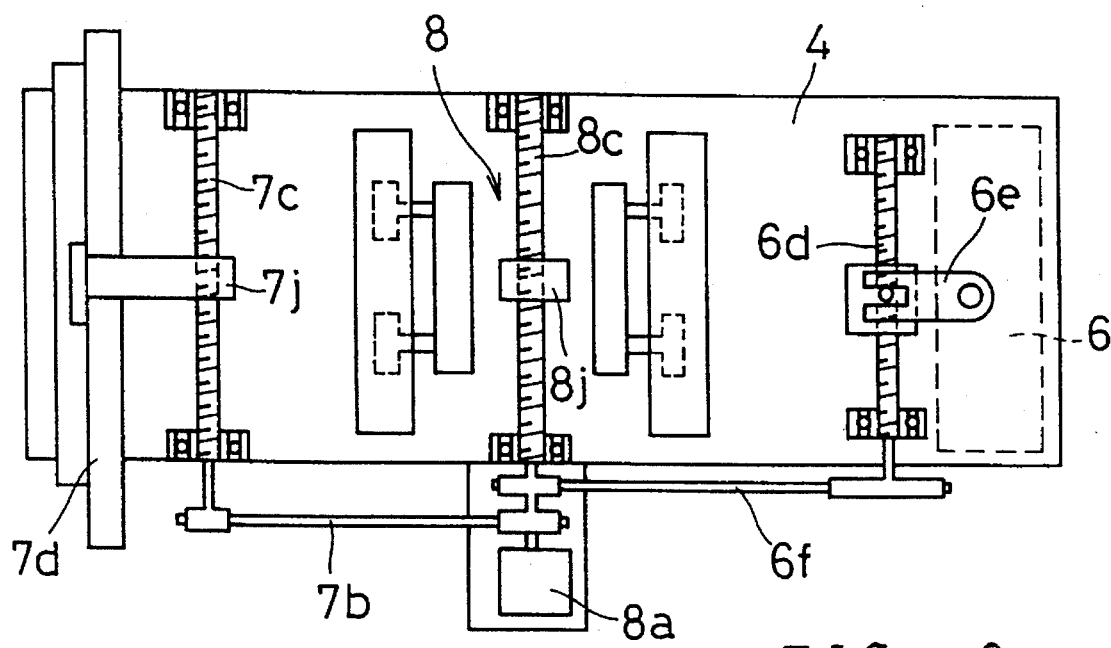

FIG. 9 shows an example wherein both the X-ray film cassette 7 and the X-ray source 6 are driven by the drive motor 8a of the linear slide mechanism 8. More particularly, the X-ray source 6 is provided with a belt mechanism 6f. With this structure, the rotation of the drive motor 8a is transmitted to the X-ray source 6 via the movement screw shaft 6d and the rotation arm 6e. The rotation angle of the X-ray source 6 is mechanically controlled in synchronization with the movement of the support arm 4.

Figure 10:
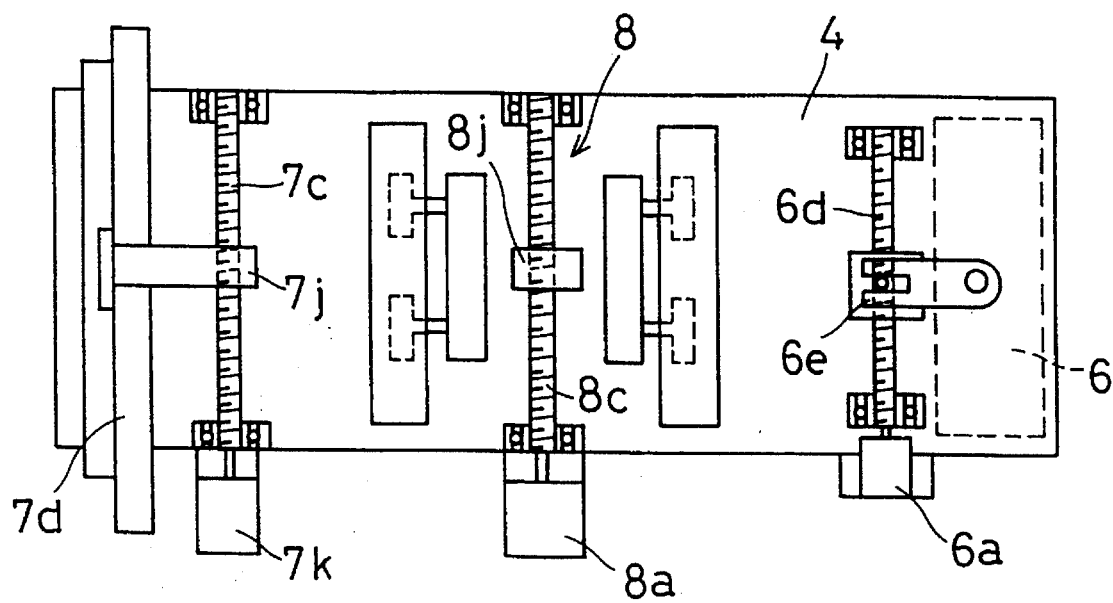

FIG. 10 shows an example wherein both the X-ray source 6 and the X-ray film cassette 7 are each provided with a drive motor. More particularly, the drive motor 8a is exclusively used to drive the linear slide mechanism 8 and a drive motor 7k is exclusively provided for the X-ray film cassette 7 to drive the movement screw shaft 7c. In addition, the rotation of the rotation motor 6a is transmitted to the X-ray source 6 via the movement screw shaft 6d and the rotation arm 6e.

In this case, the drive motor 7k of the X-ray film cassette 7 is driven at a rotation speed specifically proportional to the rotation speed of the drive motor 8a of the linear slide mechanism 8. Furthermore, the rotation speed of the rotation motor 6a of the X-ray source 6 is electrically controlled in synchronization with the movement of the X-ray film cassette 7 by such means as shown in FIGS. 6 and 7.

When the motor 7k exclusively used for the X-ray film cassette 7 is provided as described above, the X-ray film cassette 7 can be moved while the linear slide mechanism 8 remains stationary. This makes it possible to perform rotational tomographic photographing, without using the structure shown in FIG. 1, wherein the holder 7g supported by the housing 7d is moved by the drive motor 7f. However, since the apparatus is frequently used to take a plurality of tomograms on a single film by moving the X-ray film cassette 7 step by step at predetermined pitches in both planigraphic photographing and rotational tomographic photographing, a double movement structure provided with the holder 7g and the drive motor 7f should preferably be adopted for the purpose of the movement. This matter will be described later referring to FIGS. 14 and 15.

Figure 11:
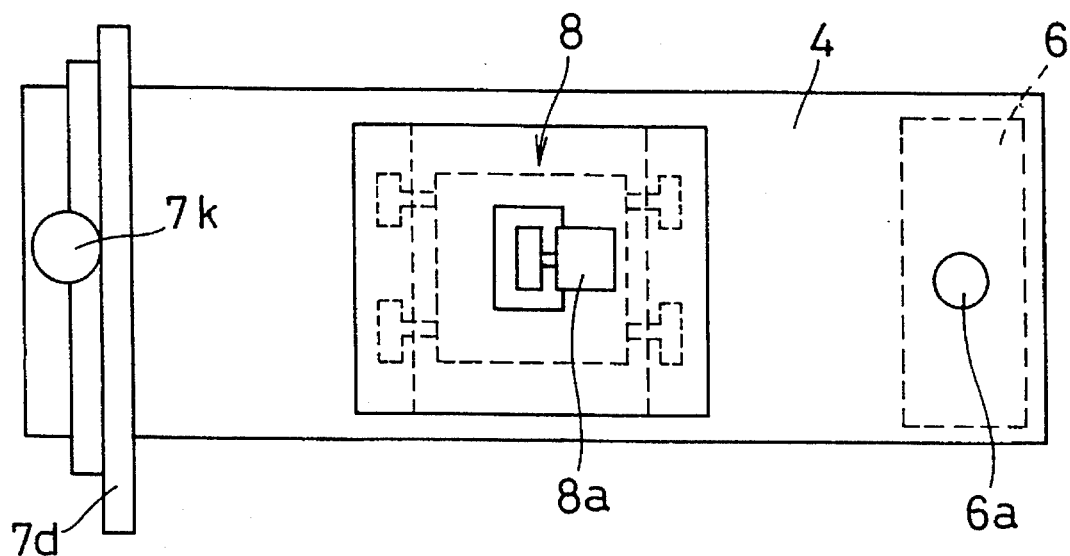

Like the example shown in FIG. 10, the example shown in FIG. 11 is provided with motors 8a, 7k and 6a that are used exclusively for the linear slide mechanism 8, X-ray film cassette 7 and X-ray source 6, respectively, but not provided with any movement screw shaft. In this case, a known mechanism, such as a mechanism for converting rotation into linear movement by using a combination of a rack and a pinion or by a system using a friction wheel, or a rotation speed reduction mechanism by using a combination of gears including worm gears, can be adopted to move the linear slide mechanism 8 and the X-ray film cassette 7 and to rotate the X-ray source 6 while keeping a predetermined relationship among them.

Figure 12:
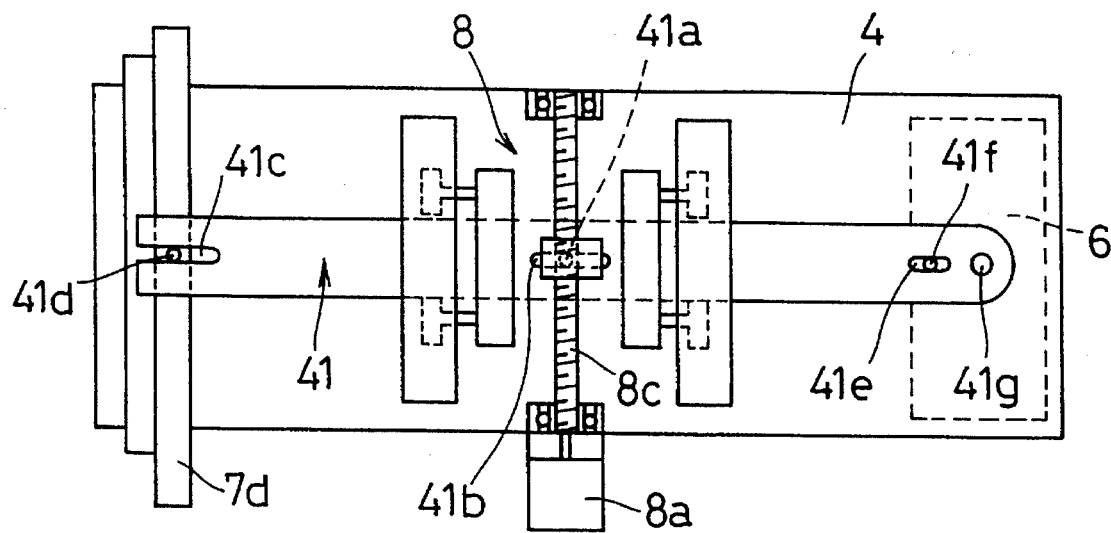

In the examples, the linear slide mechanism 8, X-ray film cassette 7 and X-ray source 6 are moved or rotated while keeping a predetermined relationship among them by using belt mechanisms or movement screw shafts, or by electrically controlling motors. Unlike these examples, the three components can be operated in synchronization with one another by using a synchronization arm for connecting the X-ray film cassette 7 and the X-ray source 6 as is shown in FIG. 12. Referring to FIG. 12, numeral 41 represents a synchronization arm. A pin 41a is disposed on a fixed member threadedly engaged with the movement screw shaft 8c of the linear slide mechanism 8 and the pin 41a is engaged with the slot 41b of the synchronization arm 41. Furthermore, a pin 41d disposed on the housing 7d is engaged with a slot 41c provided at one end of the synchronization arm 41, and a pin 41f disposed on the X-ray source 6 is engaged with a slot 41e provided at the other end.

With this structure, when the support arm 4 is moved by the motor 8a, in synchronization with this movement the synchronization arm 41 is rotated around the fulcrum 41g thereof in the direction opposite to the movement of the support arm 4. As a result, the housing 7d is moved in the direction opposite to the movement of the support arm 4. However, the X-ray source 6 is rotated in the same direction as that of the synchronization arm 41. Consequently, the X-ray irradiated from the X-ray source 6 is always incident on the same position of the X-ray film cassette 7 accommodated in the housing 7d, thereby establishing the condition for planigraphic photographing of the plane disposed at the position of the fixed pin 41a.

Figure 13:
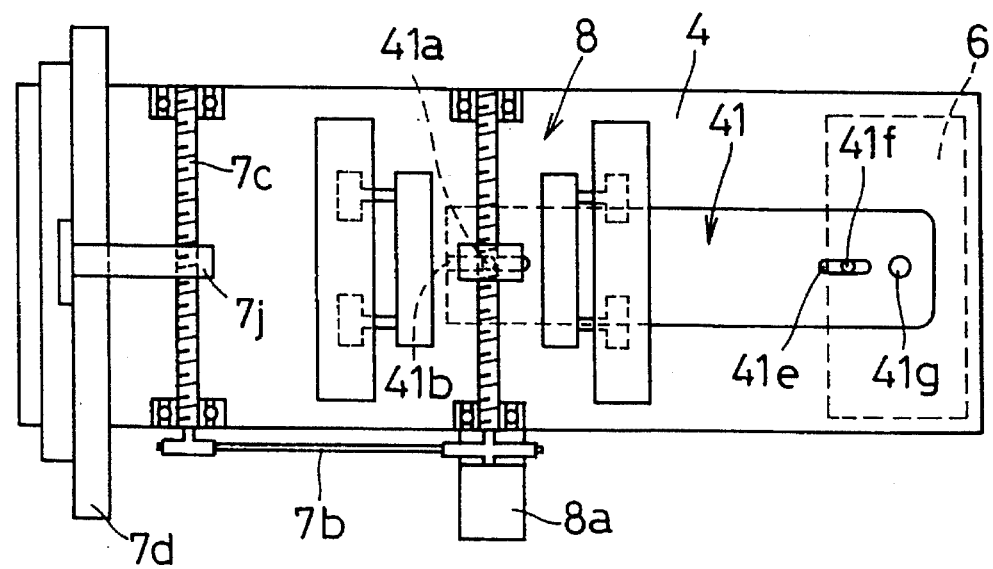

The structures shown in FIGS. 8 to 12 can be combined appropriately. FIG. 13 shows an example of such combinations, wherein a drive system using the drive motor 8a of the linear slide mechanism 8 shown in FIG. 9 is adopted on the side of the X-ray film cassette 7, and a synchronization arm system similar to that shown in FIG. 12 is adopted on the side of the X-ray source 6.

Next, the movement of the X-ray film cassette 7 and the movement of the beam-receiving shape changeover plate 7h are described below referring to FIGS. 14A, 14B and 15. The housing 7d and the beam-receiving shape changeover plate 7h are made of an X-ray shielding material. The housing 7d is provided with a rectangular opening 7m and the beam-receiving shape changeover plate 7h is provided with a wide slit 7n for planigraphic photographing and a narrow slit 7p for rotational tomographic photographing, both on the front side. The holder 7g and the X-ray film cassette 7 accommodated therein are driven by the motor 7f and the beam-receiving shape changeover plate 7h is driven by a motor 7j respectively in the lateral direction of the figure.

Figure 14A:
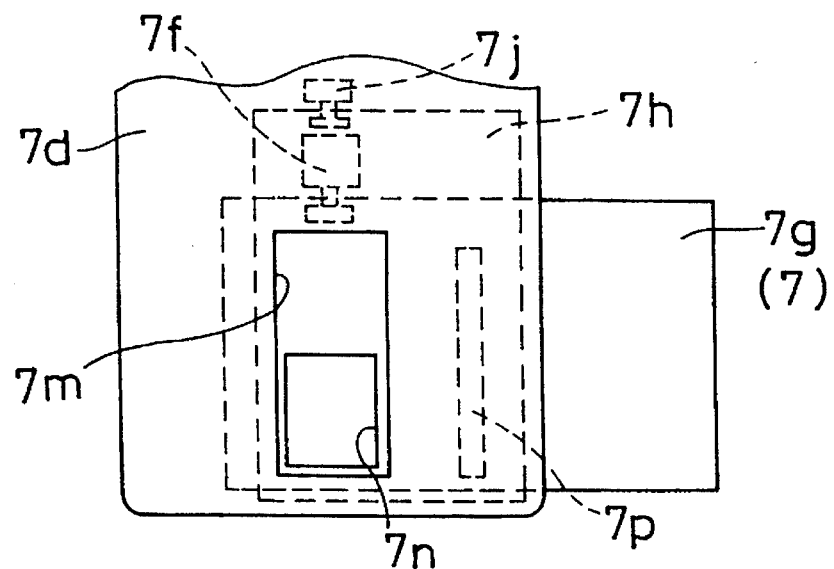
FIGS. 14A, 14B and 15 are views illustrating the movement of the film cassette and the changeover of the beam-receiving shape for the embodiment.
Figure 14B:
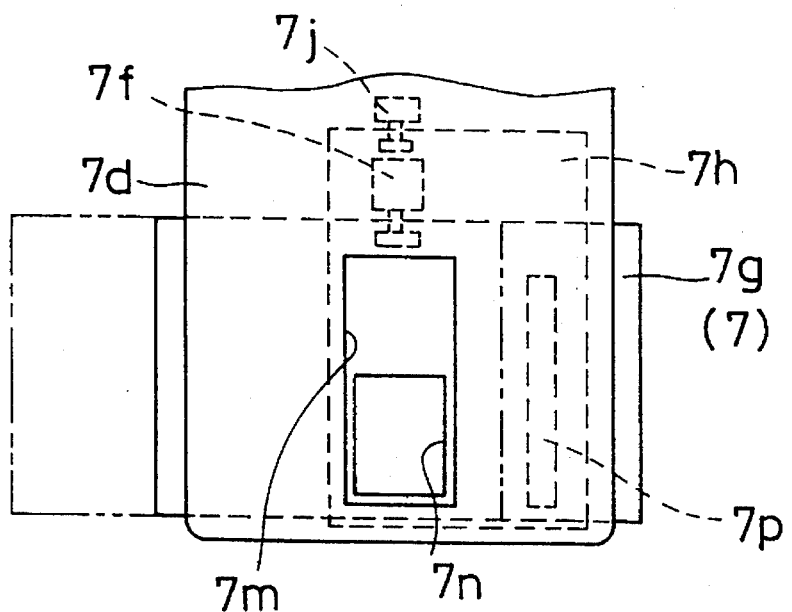
Figure 15:
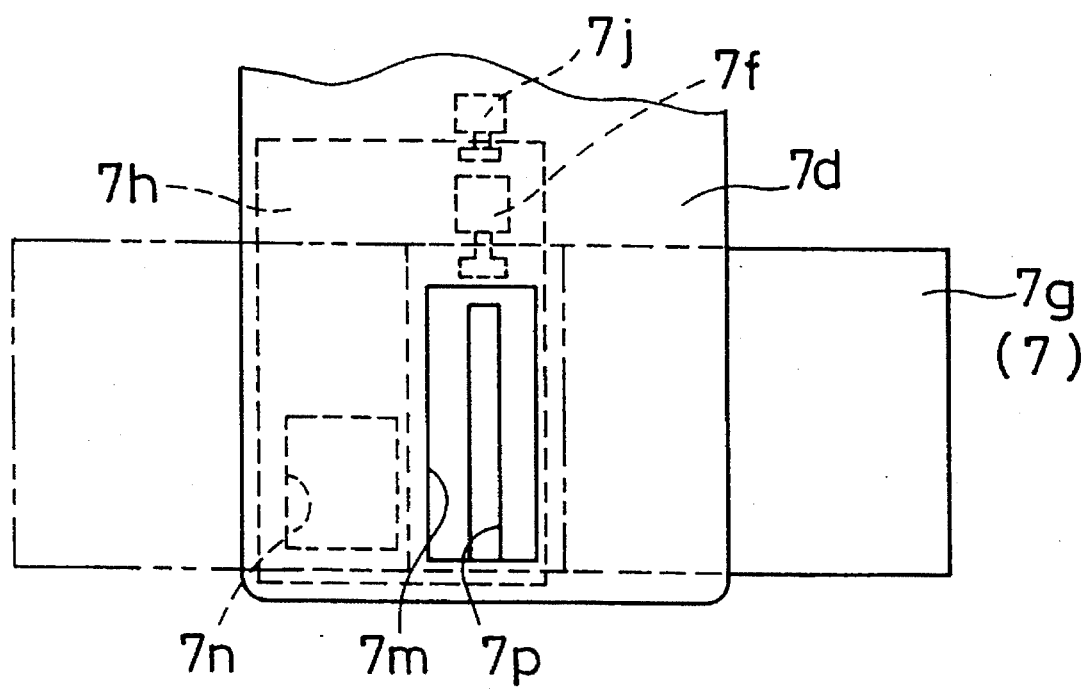

Planigraphic photographing is performed by aligning the opening 7m with the wide slit 7n as shown in FIGS. 14A and 14B and by moving the housing 7d together with the holder 7g in synchronization with the linear movement of the support arm 4. On the other hand, rotational tomographic photographing is performed by aligning the opening 7m with the narrow slit 7p as shown in FIG. 15 and by moving only the holder 7g in synchronization with the rotation of the support arm 4. In this case, a plurality of tomograms can be taken on a single film accommodated in the X-ray film cassette 7 by moving the holder 7g step by step by driving the motor 7f so that the photographing positions do not overlap. More particularly, FIG. 14A shows the photographing condition for the first layer at the time of planigraphic photographing and FIG. 14B shows the photographing condition for the second layer, wherein the holder 7g is slightly moved from the condition shown in FIG. 14A. A plurality of tomograms can also be taken on a single film at the time of rotational tomographic photographing in a way similar to that described above.

The movement of the holder 7g can also be performed by manual operation without disposing the motor 7f. The irradiation field shape changeover plate 6b of the X-ray source 6 has a structure similar to that of the beam-receiving shape changeover plate 7h. The irradiation field shape changeover plate 6b is controlled so that the X-ray beam can have a wide shape at the time of planigraphic photographing and can have a narrow slit shape at the time of rotational tomographic photographing, although this control is not shown.

As described earlier, the planigraphic X-ray apparatus of the present invention is structured by adding the linear slide mechanism 8 to a conventional rotational tomographic X-ray apparatus. The support/adjustment mechanism of the apparatus, provided with functions to support the support arm 4 and to set the position of the rotation center and direction thereof, is not limited to the combination of the X-Y table 2 and the rotation mechanism 3 used in the embodiment shown in FIG. 1. Instead of such a combination, many other mechanisms can be adopted.

Figure 16:
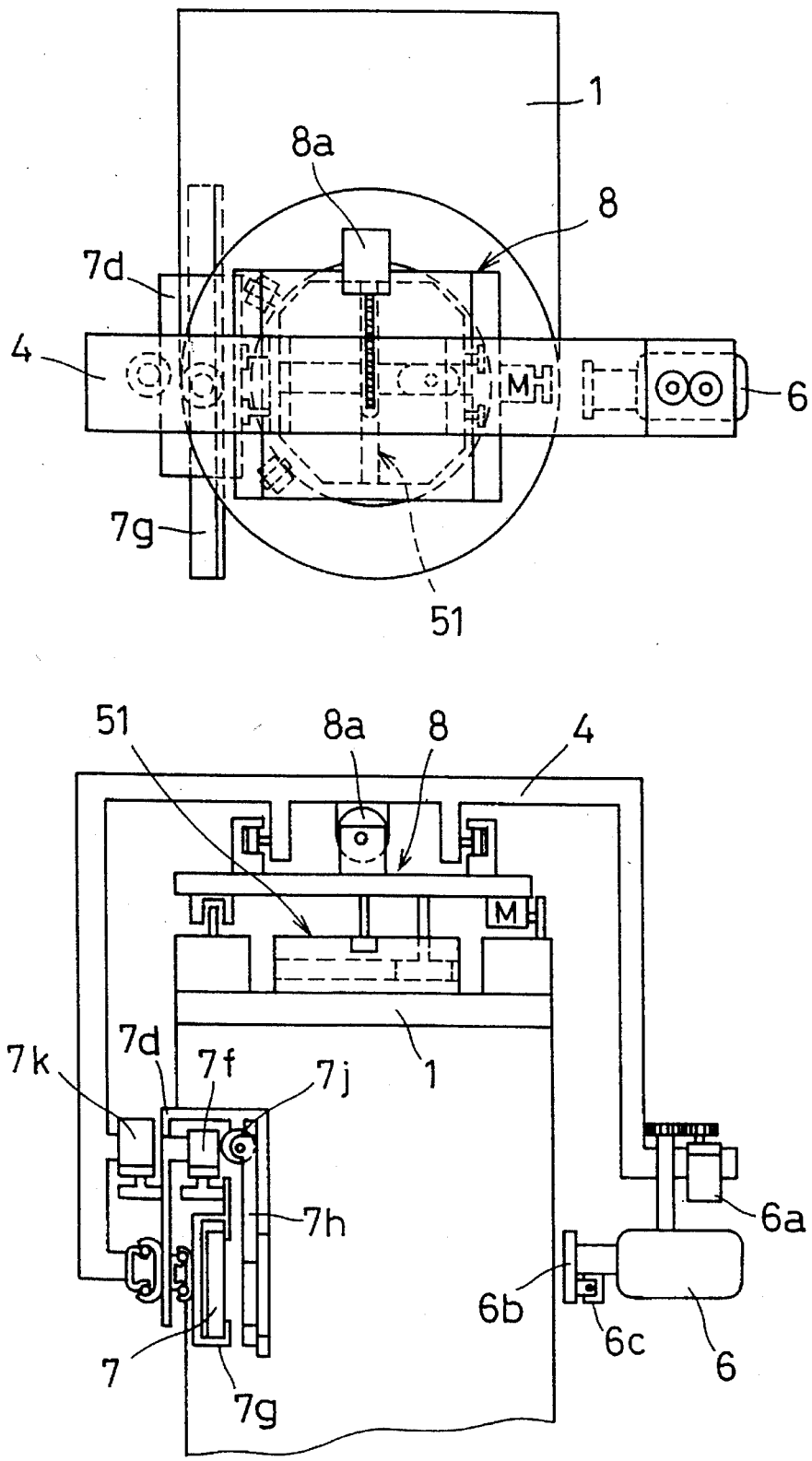
FIGS. 16 to 20 are schematic plan and side views illustrating other embodiments in accordance with the present invention.
Figure 17:
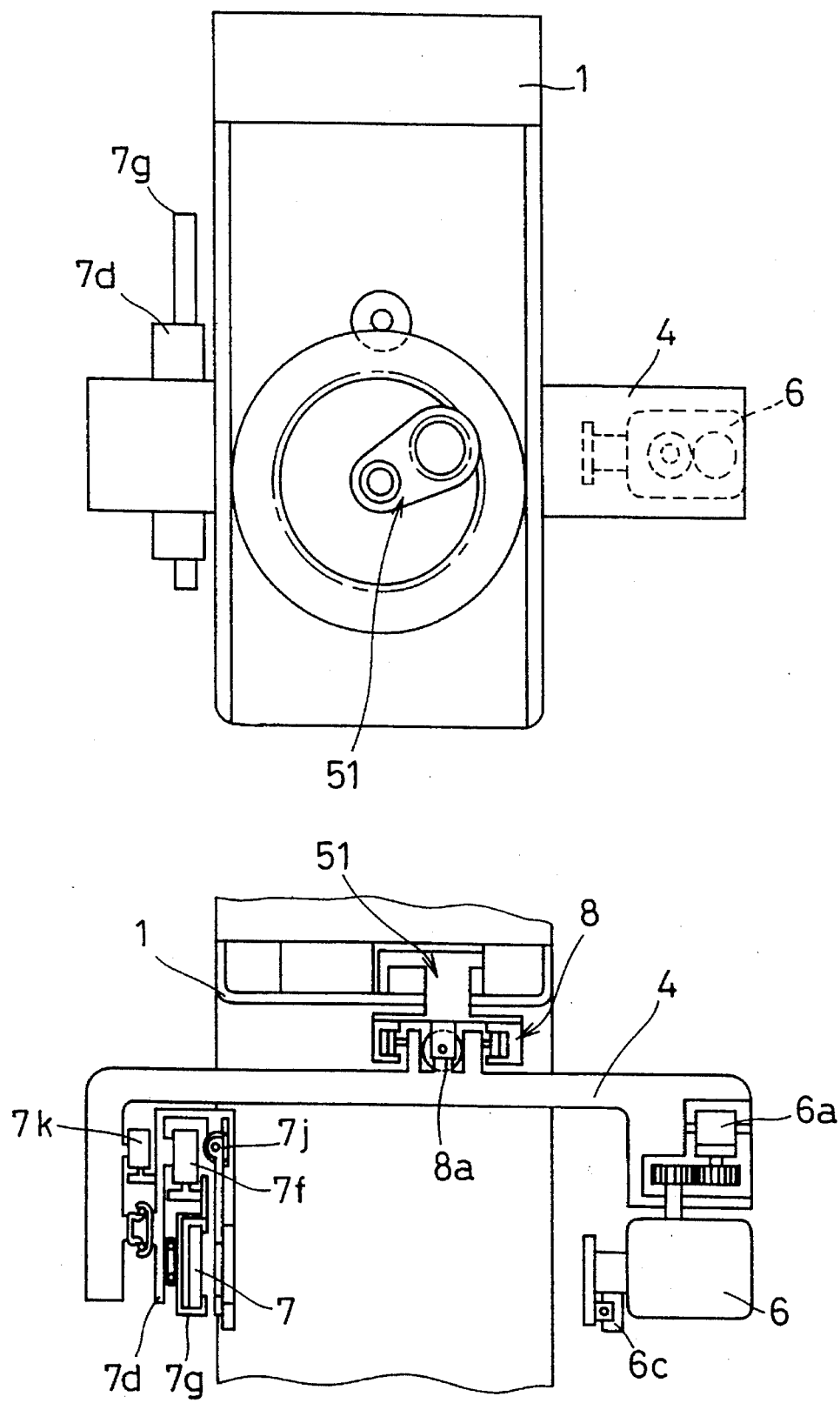
Figure 18:
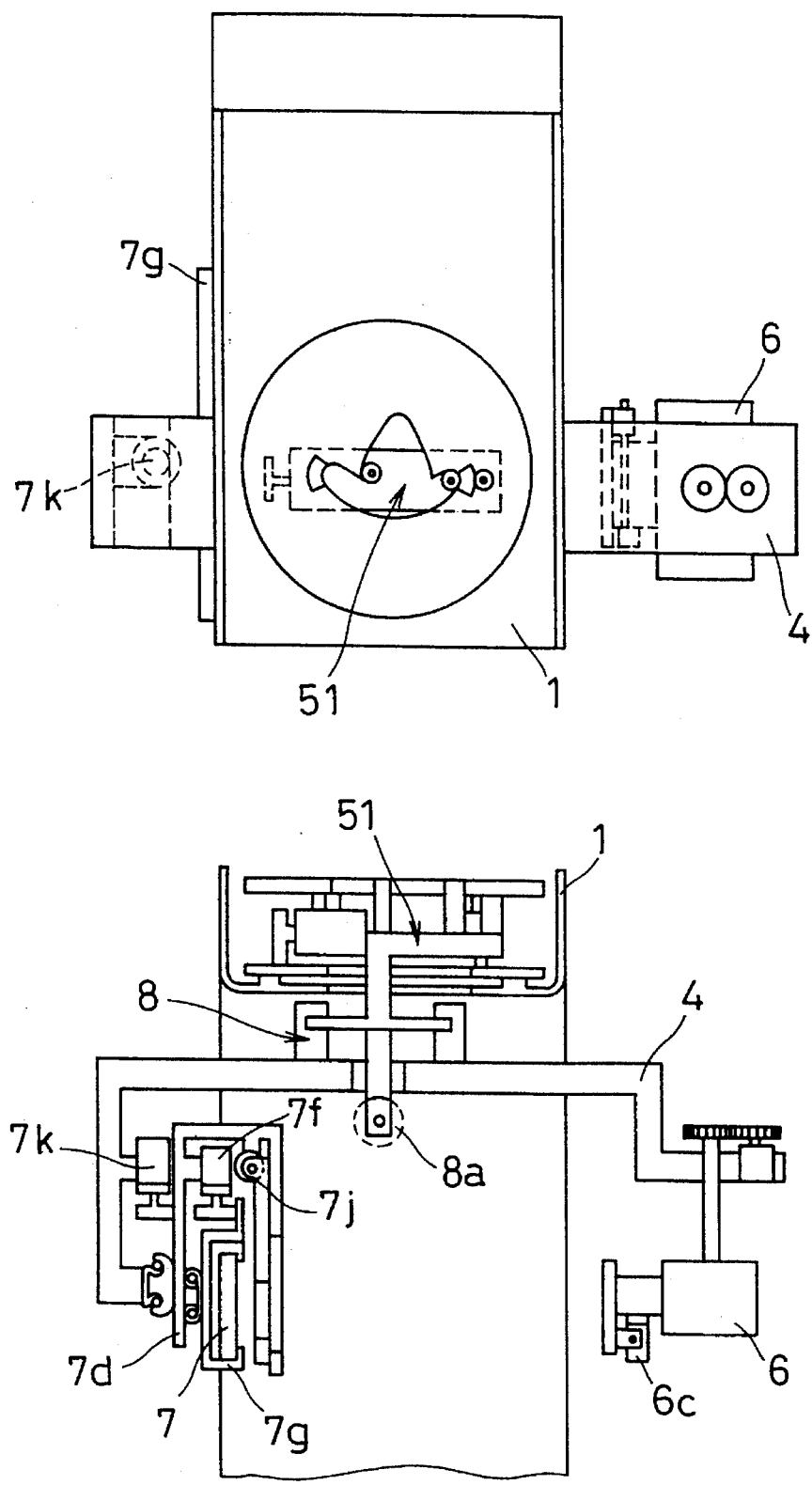
Figure 19:
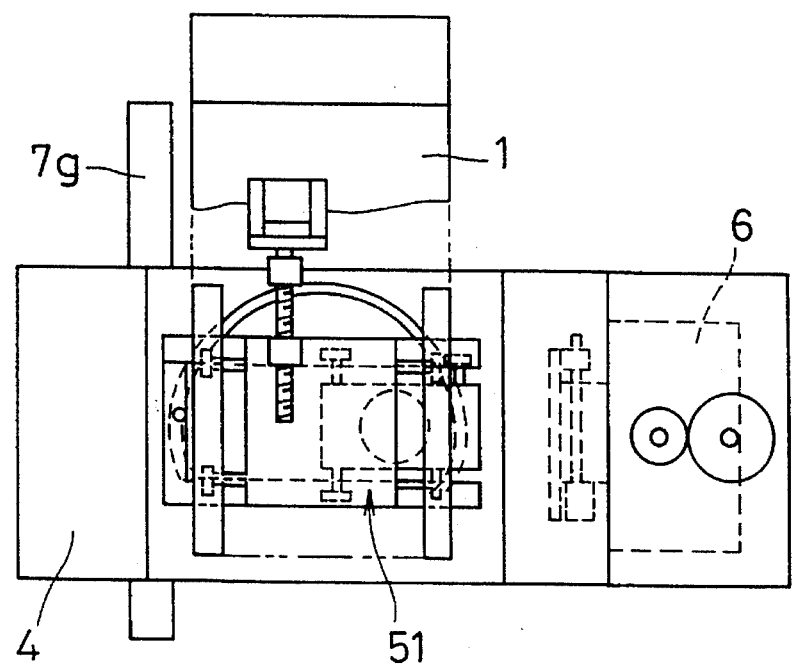
Figure 19:
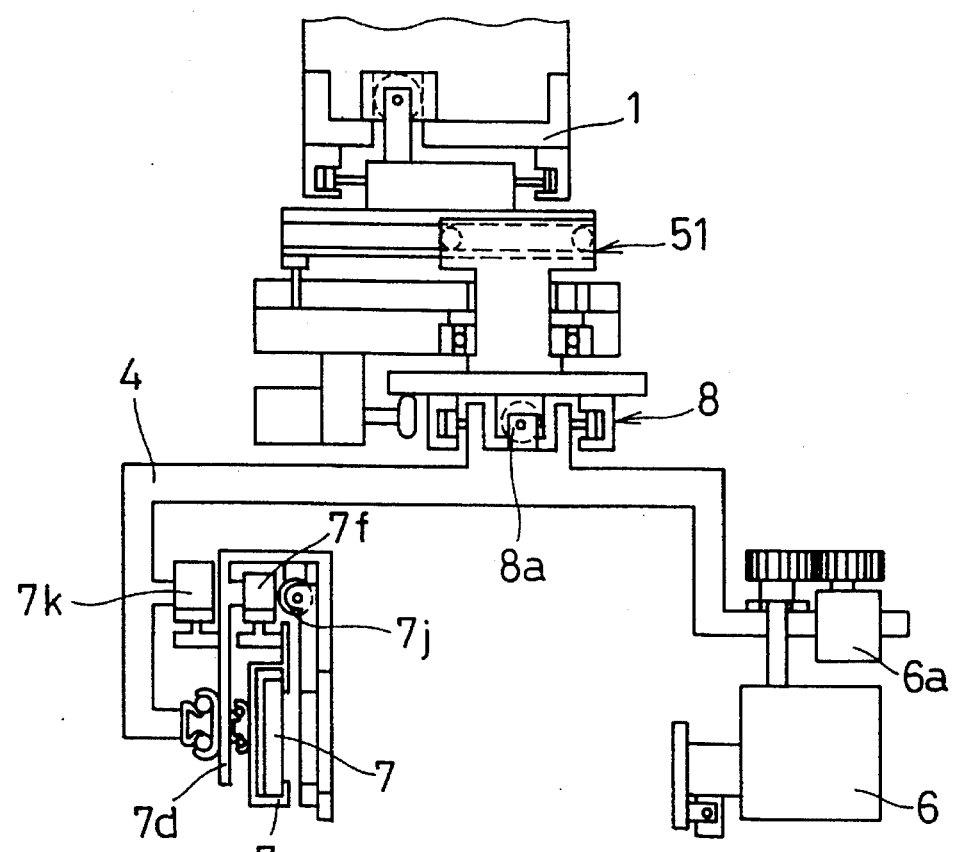
Figure 20:
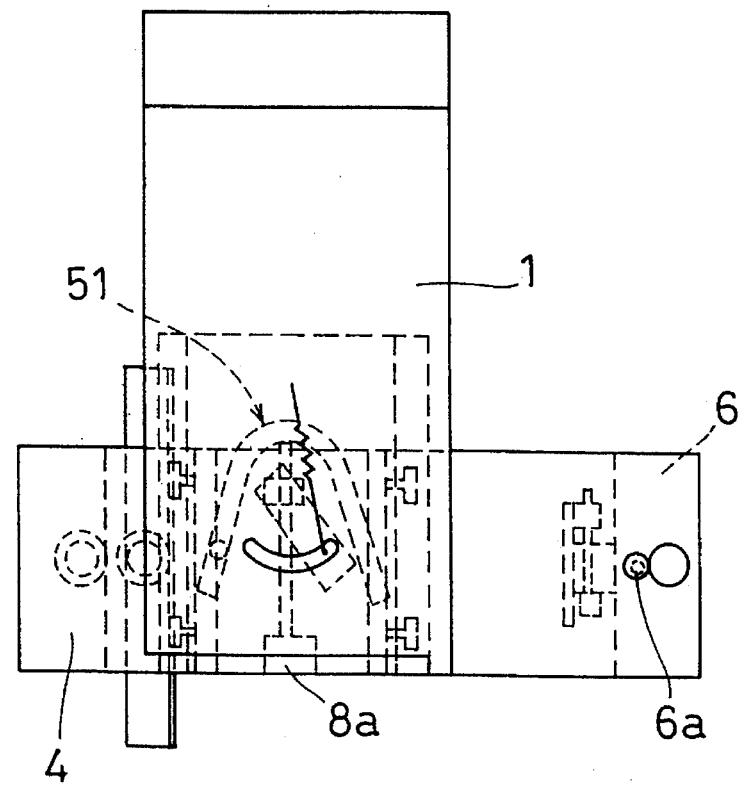
Figure 20:
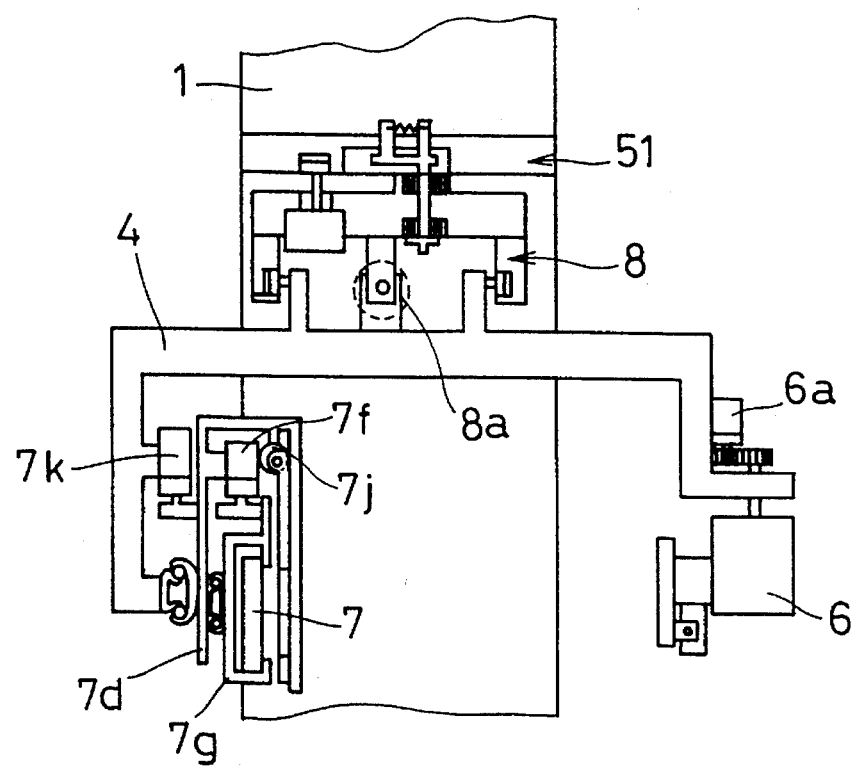

FIGS. 16 to 20 are schematic views illustrating mechanisms used as a support/adjustment mechanism 51. For example, FIG. 16 shows a mechanism of ellipsopantomography with crossing grooves, FIG. 17 shows a planetary gear mechanism and FIG. 18 shows a mechanism of three differential pivot circles tomography. These mechanisms are each used as the support/adjustment mechanism 51. FIGS. 19 and 20 also show other mechanisms used as the support/adjustment mechanism 51. In each mechanism, the linear slide mechanism 8 is provided between the support/adjustment mechanism 51 and the support arm 4. In these figures, the X-ray source 6 and the X-ray film cassette 7 are each exclusively provided with a drive motor in the same way as shown in FIGS. 10 and 11. However, it goes without saying that other drive mechanisms can be adopted appropriately.

With the structure of the present invention, the position adjustment mechanism and the rotation mechanism can be used only to set the position and direction of the support member with respect to the subject. Planigraphic photographing can be performed by simply moving the support member using the exclusively provided movement means. As a result, the operation for positioning the support member with respect to a given planigraphic plane can be performed easily and control can be simple. In addition, since the linear movement means is used only to support the weight of the X-ray generator and the X-ray detection surface, the mechanism can be made relatively compact, thereby making the entire apparatus compact and inexpensive, and yet capable of providing a planigraphic X-ray apparatus with superior operability. Furthermore, the apparatus can be easily provided with a rotational tomographic photographing function. Consequently, the present invention can offer a significantly practical apparatus capable of performing both rotational tomographic and planigraphic photographing, thereby allowing easy introduction to small clinics.

What is claimed is:

1. A planigraphic X-ray apparatus structured to obtain an X-ray image of a planigraphic plane selected to be photographed inside a subject, by using a support member which supports an X-ray generator and an X-ray detection surface disposed opposite to each other with the subject positioned therebetween, by moving said X-ray generator and said X-ray detection surface opposite to each other and parallel to the planigraphic plane while maintaining a constant relationship therebetween, by always passing the X-ray irradiated from said X-ray generator through the same specific region in tile planigraphic plane in synchronization with the movement, and by making the X-ray incident on said X-ray detection surface, comprising:

a rotation mechanism for rotating said support member to rotate said X-ray generator and said X-ray detection surface around the subject, a position adjustment mechanism for setting the position of the rotation center of said support member rotated by said rotation mechanism, a linear movement means for moving said support member in parallel to the planigraphic plane, an X-ray detection surface drive means for driving said X-ray detection surface in the direction opposite to the movement of said linear movement means in synchronization with the movement thereof, and an X-ray generator rotation means for rotating said X-ray generator toward said X-ray detection surface in synchronization with the movement of said linear movement means.

2. A planigraphic X-ray apparatus as claimed in claim 1, wherein said X-ray detection surface drive means is used to drive said X-ray detection surface by transmitting the rotation of the drive motor of said linear movement means via a mechanical synchronization mechanism.

3. A planigraphic X-ray apparatus as claimed in claim 1, wherein said X-ray detection surface drive means is used to drive said X-ray detection surface by using a motor driven at a rotation speed specifically proportional to the rotation speed of the drive motor of said linear movement means.

4. A planigraphic X-ray apparatus as claimed in claim 1, wherein said X-ray generator rotation means is used to drive said X-ray generator by transmitting the rotation of the drive motor of said linear movement means via a mechanical synchronization mechanism.

5. A planigraphic X-ray apparatus as claimed in claim 1, wherein said X-ray generator rotation means detects the position of said X-ray detection surface and the rotation angle or said X-ray generator with respect to said support member and said X-ray generator is rotated by a rotation motor so that a predetermined relationship can be obtained between the detected position and angle.

6. A planigraphic X-ray apparatus as claimed in claim 1, wherein said X-ray generator rotation means detects the position of said X-ray detection surface with respect to said support member and rotates said X-ray generator by driving said rotation motor so that a predetermined rotation angle calculated from the detection position can be obtained.

7. A planigraphic X-ray apparatus as claimed in claim 3, wherein said X-ray generator rotation means detects the position of said X-ray detection surface with respect to said support member and rotates said X-ray generator by driving said rotation motor so that a predetermined rotation angle calculated from the detection position can be obtained.

8. A planigraphic X-ray apparatus as claimed in any one of claims 1 to 7, wherein said apparatus is structured to obtain an X-ray image of a rotational tomographic plane selected to be photographed inside the subject, without activating said linear movement means for moving said support member and said X-ray generator rotation means for rotating said X-ray generator, by rotating said support member by said rotation mechanism to rotate said X-ray generator and said X-ray detection surface around the subject, by controlling the position of the rotation center of said support member rotated by said position adjustment mechanism and by moving said X-ray detection surface in the direction approximately perpendicular to the direction of the X-ray irradiated from said X-ray generator in synchronization with the rotation of said support member.

* * * * *